United States Patent [19]

Sevoian

[11] 3,981,771
[45] Sept. 21, 1976

[54] MAREK'S DISEASE VACCINE
[76] Inventor: Martin Sevoian, 167 Montague Road, North Amherst, Mass. 01059
[22] Filed: May 29, 1975
[21] Appl. No.: 581,967

Related U.S. Application Data
[63] Continuation-in-part of Ser. No. 380,615, July 19, 1973, abandoned.

[52] U.S. Cl. ................................. 195/1.3; 424/89
[51] Int. Cl.² ................................. A61K 39/32
[58] Field of Search ................. 424/89; 195/1.3

[56] References Cited
UNITED STATES PATENTS

| | | | |
|---|---|---|---|
| 3,444,293 | 5/1969 | Hudson | 424/89 |
| 3,548,055 | 12/1970 | Moulthrop | 424/89 |
| 3,590,128 | 6/1971 | Larose | 424/89 |
| 3,642,574 | 2/1972 | Okazaki et al. | 195/1.5 |
| 3,674,861 | 7/1972 | Churchill | 424/89 |
| 3,783,098 | 1/1974 | Calnek et al. | 195/1.1 |

OTHER PUBLICATIONS

Witter et al., Avian Diseases, 12:169–185, Feb. 1968.
Witter et al., Avian Diseases 13:101–118, 171–184, Feb. 1969.
Kottaridis World's Poultry Sci. Jl. 25(1):35–45, Jan.–Mar. 1969.
Churchill et al., Nature 221:744–747, Feb. 22, 1969.

*Primary Examiner*—Shep K. Rose

[57] ABSTRACT

A vaccine for immunizing poultry against Marek's disease (Type II leukosis), processes for producing same, and methods of immunizing poultry flocks. The vaccine is obtained by modifying the JM strain of Marek's disease by rapid serial passage through selected tissue of live chickens until highly virulent followed by attenuation thereof in avian embryos.

5 Claims, 4 Drawing Figures

MAREK'S DISEASE VACCINE

This is a continuation-in-part of my copending application Ser. No. 380,615, filed July 19, 1973, now abandoned.

BACKGROUND OF THE INVENTION

1. Field of the Invention

This invention relates to vaccines for immunizing poultry against Marek's disease (Type II leukosis), and specifically to vaccines which are immunogenic and non-pathogenic for Marek's disease, methods of producing such vaccines, and methods of immunizing poultry flocks therewith.

Neoplasia is one of the most common pathologic manifestations found in poultry. The vast majority of avian tumors have their histogenesis in the hematopoietic system and have been classified as the Avian Leukosis Complex. At least two distinct virus types, i.e., a RNA virus (sometimes called RIF virus), and a DNA herpes virus (of which the JM virus was first isolated from chickens as a prototype), can cause leukotic tumors. The etiologic separation and identification of these diseases has led to the terms of lymphoid leukosis, or Type I lymphoid leukosis, for the RNA virus tumors, and Marek's disease, or Type II lymphoid leukosis, for the DNA virus tumors.

The majority of naturally occurring tumors in poultry are Marek's disease types. Currently, the annual losses due to poultry tumors are estimated at 200 million dollars in the U.S.

Marek's disease infections in poultry populations are both common and widespread. Nearly all field flocks are infected to some degree. Most chickens become infected at an early age and remain so chronically. Though infection levels are as high as 100 percent in most cases, neoplasia resulting from such infections may range from a negligible amount in some flocks to well over 50 percent in other flocks.

2. Description of the Prior Art

Much research has been devoted to developing treatments and preventions for Marek's disease, but until recently no satisfactory vaccine was available.

U.S. Pat. No. 3,642,574 describes a vaccine produced from turkey herpes virus (HVT) which is non-pathogenic in chickens and protects, by mechanisms as yet unexplained, vaccinated chickens against development of Marek's disease tumors.

The vaccine described in U.S. Pat. No. 3,642,574 gained immediate and widespread acceptance as soon as it was available to poultry raisers, due to the seriousness of the disease and the unavailability of any effective alternative treatment.

However, the HVT vaccine has recently become suspect as a satisfactory solution to the Marek's disease problem because its effectiveness in preventing tumor development currently appears in many cases to be less than originally reported. This may be due to the fact that HVT vaccine does not produce significant levels of protective or neutralizing antibodies against field infections. It has been determined that inoculating chickens with HVT vaccine results in a chronic viremia, as distinguished from an immunity which depresses or eradicates the infection. Furthermore, chickens vaccinated with HVT vaccine are not immune to a super-infection to Marek's disease virus, and the protection provided by the HVT vaccine is more "cosmetic" than real. Furthermore, original reports that HVT did not grow in mammalian cells have now been questioned.

U.S. Pat. No. 3,590,128 describes a vaccine for the Type I lymphoid leukosis, as distinguished from a Marek's disease vaccine.

U.S. Pat. No. 3,674,861 to Churchill describes an attenuation of any strain of Marek's disease vaccine produced by serial passage of field Marek's disease virus in avian cells. The virus attenuated by Churchill was obtained from infected field birds and includes the HPRS - 16 strain and JM strain. Churchill's objective was to rid the Marek's disease virus of the A-antigen.

It is apparent from the above that there is a tremendous need for an effective vaccine against Marek's disease, and particularly for such a vaccine that will prevent and/or eradicate Marek's disease infection in a vaccinated chicken.

SUMMARY OF THE INVENTION

According to the present invention, a vaccine is provided which when properly administered is immunogenic and non-pathogenic for Marek's disease in poultry, and particularly chickens.

A virulent strain of Marek's disease virus identified as JM-V strain or agent was developed as will hereinafter be more fully described by rapidly passing JM virus in cells found in certain organ tissue of live chickens for several hundred passages. This JM-V strain is extremely pathogenic in chickens.

It was observed that day-old chickens which received a large dose of JM-V strain usually succumbed. However, when a smaller dose of JM-V strain was administered, some chickens survived and developed from 1,000 to 10,000 neutralizing antibody doses to JM virus. These surviving birds with high antibody levels were relatively immune to later exposure to JM virus, but the use of JM-V strain is not considered to be an acceptable method of immunization because of the extreme pathogenic nature of the JM-V strain.

A vaccine, to be satisfactory, should first of all be safe as to the vaccinated bird. It should also produce high levels of neutralizing antibodies, such that the viremia resulting from the vaccination is temporary, in order that the vaccinated bird may be aviremic when slaughtered for food purposes.

The vaccine according to this invention meets the above criteria.

A sample of the virulent JM-V strain of Marek's disease virus (identified as JM-V agent or strain) has been deposited as a culture of the living organism under the designation No. VR-736 with the American Type Culture Collection, 12301 Parklawn Drive, Rockville, Maryland 20852. The organism will hereinafter be referred to as JM-V agent or strain No. VR-736. As mentioned previously, this organism is immunogenic but extremely pathogenic for poultry.

The JM-V agent grows well in avian embryos. A method of modifying the agent in accordance with this invention to make it nonpathogenic for chickens involves serially passing it through the yolk sac of avian embryos. Beginning with blood from a moribund chick previously inoculated with JM-V, about 0.1 ml. of this blood is placed within the yolk sac of a 4-to-6 day old avian embryo. About 7 days post-inoculation 0.1 ml. of yolk from the infected embryo is removed and serially re-passed into a fresh 4-to-6 day old avian embryo. This procedure is repeated for about 40 passages. Harvests of modified material from the advanced passaged infected embryos are highly antigenic, producing protective antibodies in chicks against Marek's disease virus (JM strain), and will protect chickens against field infections.

The harvested material from the advanced passages may be stabilized with SPGA or other suitable stabilizer and frozen in liquid nitrogen until shortly before use, at which time it will be diluted with a pharmaceutically acceptable carrier according to titer and desired dosage. The harvested material may alternatively be lyophilized by standard known procedures.

The harvested material containing modified agent derived from JM-V, whether frozen or lyophilized as described above, may be diluted with a pharmaceutically suitable carrier, such as phosphate buffered saline or tryptose phosphate broth which may contain Arlacel A, Bayal F, Freunds, etc., before administration to poultry. The diluted material may be injected via a parenteral route or otherwise administered to chickens from day-old to maturity depending on the results desired and the type of flock under consideration. For example, as will be described in more detail later, adult female chickens may be actively immunized with the vaccine of this invention, and they will pass congential protective antibodies to their offspring, negating the necessity of vaccinating the offspring individually where the offspring are intended as broilers, which are slaughtered at about seven weeks of age. The congenital antibodies are only effective for three to five weeks, but the short time between loss of congenital immunity and slaughter is insufficient for significant tumor development.

My invention involves the development of a modified strain of Marek's disease by multiple passage of the JM strain of field Marek's disease through selected tissue of live chickens to obtain a highly pathogenic and immunogenic (JM-V agent or strain No. VR-736) of virus which is then attenuated to a non-pathogenic but highly immunogenic vaccine.

It is an object of the invention to provide an effective vaccine for Marek's disease in poultry.

It is a further object to provide such a vaccine which is safe (non-pathogenic) and which results in an aviremic vaccinate.

That the above and other objects and advantages are obtained by the present invention will become apparent from consideration of the following detailed description of the preferred embodiments thereof.

Figure 1:
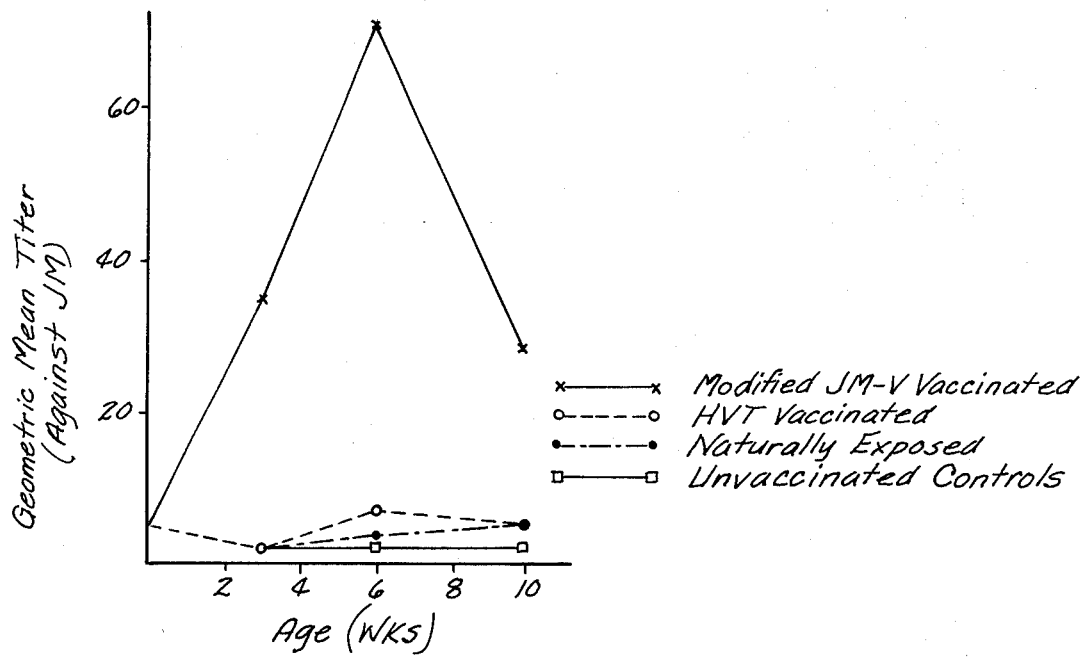
FIGS. 1–4 are graphical depictions of test results showing the antibody response resulting from use of the vaccine in accordance with this invention.

In accordance with this invention, a vaccine is produced which when properly administered is immunogenic and non-pathogenic for Marek's disease in poultry, particularly chickens. The previously isolated JM virus widely reported in literature and the patents, referred to above, is characterized as a poor immunogen and is chronically infectious to chickens. Other known strains of Marek's disease virus behave in a similar manner. My invention avoids using the known Marek's virus strains and instead involves the development of a modified JM virus which is characterized as both highly immunogenic and not chronically infectious. I postulated that by selecting particular organ tissue of young chicks infected with the JM strain that the incidence of lymphoblast in these organs would by serial passage in live chicks result in a selection of immunogenic cells, i.e., cellular elements of the reticulo-endothelial system and thus the production of humoral antibodies. Work was commenced in 1962 by extracting the spleen, bone marrow, liver and kidneys of young chicks infected with JM Marek's disease infection. These organs were ground up and suspended in physiological saline solution an inoculated intraperitoneally or intra-abdominally in 16, day-old chicks. One chick developed tumors after 13 days post inoculation and its organs were used for the next passage in eight, day-old chicks. From one passage to the next, the organs used, i.e., spleen, bone marrow, liver and kidneys, were taken from one or more of the chicks which had developed lesions or had become moribund. After the first 25 such passages, whole blood extracted from the moribund chickens was serially passaged through usually ten or more day-old chicks for about 400 passages. From Table I, it will be seen that after 146 passages, 100 percent chick mortality occurred within 6 days post inoculation and that after 400 days 100 percent mortality occurred within 5 days. It was thus established that a highly virulent, indeed lethal strain of the JM virus was produced, which I identified as JM-V. When administered parenterally as whole blood inoculum, the lethal dose 50 percent in most genetic strains of chicks is $10^6$ per cc., with injected birds succumbing to a lymphoproliferation within 3 to 6 days post-inoculation.

It was found, however, that chickens which were given a sub-lethal, but infective, dose of JM-V agent (No. VR-736) and survived produced neutralizing antibodies against field Marek's disease viruses. Even though it was shown that the virulent JM-V agent (VR-736) produced high levels of neutralizing antibodies, it was apparent that modification of this virulent agent was needed to produce a safe vaccine.

It was also found that a cell-free product prepared by sonicating whole blood infected with JM-V, followed by centrifugation and filtration through a 0.45 micron Millipore filter could produce neutralizing antibodies in birds. Cell-free material so-prepared did in fact provide protection to surviving birds against subsequent JM challenge, but a substantial percentage of birds inoculated with this cell-free material died as a result of the inoculation, so that cell-free JM-V (unmodified) was not considered to be acceptable as a vaccine against Marek's disease. Thus, it was again apparent that in order for a satisfactory vaccine to be obtained some manner of reducing the pathogenicity of the JM-V agent was required.

JM-V agent No. VR-736 (0.1 ml of whole blood from a moribund chick) was injected into the yolk sacs of 4-to-7 day old avian embryos, and then harvested 7 days post-inoculation and repassed into avian embryros (in vivo).

TABLE I

EFFECTS OF RAPID PASSAGED JM STRAIN VIRUS IN CHICKS

| PASSAGE NUMBER | NO. CHICKS INOC. | 1 | 2 | 3 | 4 | 5 | 6 | 7 | 8 | 9 | 10 | 11 | 12 | 13 | 14 | 15 | 16 | 17 | 18 | 30 | MORT. TOTAL |
|---|---|---|---|---|---|---|---|---|---|---|---|---|---|---|---|---|---|---|---|---|---|
| 1 | 16 | | | | | | | | | | | | | 1L* | | | | | | | 0/16 |
| 2 | 8 | | | | | | 2L* | | | | | | | | | | | | | | 0/8 |
| 3 | 10 | | | | | | | | | | | | | | | | | | | 1L* | 0/10 |
| 4 | 20 | | | | | | | | 1* | 2 | | | 3 | 1 | 1 | | | | 1 | | 9/20 |
| 5 | 10 | | | | | | | | 1 | 2* | 2 | 1 | | | | | | | 1 | | 7/10 |
| 10 | 10 | | | | | | | | 2* | 2 | 2 | 1 | 1 | | | | | | | | 8/10 |
| 15 | 8 | 1 | | | | | | | | | | 1* | 1 | 1 | | 1 | | 1 | 1 | | 7/8 |
| 20 | 10 | | | | 1 | 5 | 1* | 2 | 1 | | | | | | | | | | | | 10/10 |
| 25 | 10 | | | 1 | | 2 | 4* | 1 | | | | | | 1 | 1 | | | | | | 10/10 |
| 146 | 10 | | | 1 | 3* | 6 | | | | | | | | | | | | | | | 10/10 |
| 400 | 10 | | 3 | 4* | 3 | | | | | | | | | | | | | | | | 10/10 |

L Lesions, no mortality
*Used for Repassage

After a sufficient number of repassages, at least about 40, the agent was found to be modified to the point where it was no longer pathogenic for chickens. Surprisingly, it was found that the modified non-pathogenic agent retained its highly immunogenic character, such that the modified agent is extremely useful as a vaccine against Marek's disease. The resulting vaccine, I have designated JMV-A, which, while lethal for embryos is non-pathogenic for chickens. Moreover, this JMV-A vaccine is highly immunogenic, non-chronic and non-contagious as compared with vaccines produced by use of the JM strain.

The number of passages necessary to produce a non-pathogenic vaccine derived from JM-V agent (VR-736) has not been precisely determined, as the change from pathogenic or non-pathogenic is both gradual and imprecise. However, after 10 repassages the pathogenicity is considerably reduced, and after at least about 40 repassages the agent appears to be adequately modified. About 50 repassages are recommended for additional safety. A required number of passages is that number which provides a non-pathogenic vaccine, as contrasted to the pathogenic JM-V starting material.

There have been negligible losses to Marek's disease in approximately 2,000 chickens vaccinated with the JMV-A agent obtained by 50 passages of JM-V through chick embryos and challenged with Marek's disease virus, whereas losses were considerable in chickens vaccinated with HVT vaccine and similarly challenged.

The above is illustrated in the following Table II, in which the effects of JM and JM-V (Agent No. VR-736) challenges are shown for separate groups of day-old chicks, one group of which was vaccinated by injection of 2,000 plaque forming units of HVT vaccine, and the other group of which was injected with 10 $CEID_{50}$ of the vaccine of this invention which was obtained by 50 passages of Agent No. VR-736 through avian embryos, resulting in the modified non-pathogenic but highly immunogenic material. Recommended dose for commercial HVT vaccine is 1,000 plaque forming units.

TABLE II

| TREATMENT | CHALLENGE AT 2 WEEK POST VACC. | |
|---|---|---|
| | JM-V ($10^3$CLD) affected/total | JM ($10^3$CID) affected/total |
| HVT Vaccine | 16/20 | 8/20 |
| Modified JM-V Vaccine (50 passages through avian embryos) | 0/20 | 1/20 |

TABLE II-continued

| TREATMENT | CHALLENGE AT 2 WEEK POST VACC. | |
|---|---|---|
| Controls | 20/20 | 20/20 |

In the above table, a test chicken was considered "affected" if it either died or manifested lymphoproliferative lesions of Marek's disease. CLD, CID and CEID refer respectively to chick lethal dose, chick infective dose and chick embryo infective dose.

The vaccine of this invention may also be used to vaccinate brood birds, and the birds will pass a congenital immunity to their offspring which lasts for 3 to 5 weeks on the average, at which time they have become immunologically competent to better handle field infections of Marek's disease. Since broilers are usually slaughtered at about 7 to 8 weeks of age, the broilers will not have time before slaughter to develop significant tumors even if they should become infected with Marek's disease after the congenital immunity wears off.

A preferred plan for immunizing poultry flocks where the birds are to be kept past a few weeks of age is to vaccinate dams parenterally with, for example, 100 $CEID_{50}$ of the vaccine of this invention, and to also vaccinate offspring a day-old or so to provide lasting immunity after congenital immunity wears off. An additional vaccination of the offspring at about three weeks of age or sometime thereafter reinforces the immunity.

The following TABLE III shows the effects of passive (maternal) antibodies on cell-free JM virus challenge of progeny chicks from dams vaccinated with 100 $CEID_{50}$ of cell-free JM-V material compared to chicks from dams vaccinated with 5,000 plaque forming units of commercially available HVT vaccine, and also chicks from unvaccinated dams. The challenge in each case was 0.1 ml. of JM virus ($10^{4.8}$ $CID_{50}$ per cc.) at the indicated dilution. As is apparent from the data tabulated below, the cell-free JM-V material was much more effective in providing passive immunity to offspring of vaccinated dams then was the commercial HVT vaccine. Also, the JM virus reisolations showed that the virus levels in chicks from dams vaccinated with the cell-free JM-V material were negligible compared to the HVT vaccinated group. This dramatically illustrated the antibody response obtainable from JM-V material. As discussed above, however, the cell-free JM-V is not completely safe, and even though surviving birds are protected, a certain percentage succumb to Marek's disease upon being vaccinated with unmodified JM-V.

The point concerning safety of vaccine according to the invention versus unmodified cell-free JM-V material is effectively illustrated by the following Table IV, which shows the survival figures for chicks vaccinated at one day of age, followed by booster vaccination at three weeks, with unmodified cell-free JM-V compared to survival figures for chicks vaccinated with the vaccine of this invention.

to unvaccinated controls. In all cases, the numbers represent survivors/birds tested.

TABLE V

|        | Cell-Free JM-V | Embryo-Passaged Material | HVT | Natural Exposure to Infected Chicks | Unvaccinated Controls |
|--------|----------------|--------------------------|-----|--------------------------------------|-----------------------|
| N-Line | 6/6            | 6/6                      | 5/6 | 3/6                                  | 3/6                   |
| P-Line | 6/6            | 6/6                      | 5/6 | 1/6                                  | 2/6                   |

The immune response (serum neutralization titers)

TABLE III

| Group | Challenge Dilution of JM Virus | Affected/Total* | | Infected/Total** | | Plaques/$2 \times 10^6$ cells*** | |
|---|---|---|---|---|---|---|---|
| | | P | N | P | N | P | N |
| Vaccinated parenterally with 100 $CEID_{50}$ of cell-free JM-V | $10^0$ | 1/5 | 1/5 | 3/3 | 3/3 | 12 | 10 |
| | $10^{-1}$ | 0/5 | 0/5 | 0/3 | 0/3 | 0 | 0 |
| | $10^{-2}$ | 0/5 | 0/5 | 0/3 | 0/3 | 0 | 0 |
| | $10^{-3}$ | 0/5 | 0/5 | 0/3 | 0/3 | 0 | 0 |
| | $10^{-4}$ | 0/5 | 0/5 | 0/3 | 0/3 | 0 | 0 |
| | Non-inoculated control | 0/5 | 0/5 | 0/3 | 0/3 | 0 | 0 |
| Vaccinated parenterally with 5,000 PFU of commercial HVT vaccine | $10^0$ | 4/5 | 3/5 | 3/3 | 3/3 | 28 | 27 |
| | $10^{-1}$ | 4/5 | 2/5 | 3/3 | 3/3 | 27 | 18 |
| | $10^{-2}$ | 3/5 | 1/5 | 3/3 | 3/3 | 21 | 12 |
| | $10^{-3}$ | 2/5 | 0/5 | 3/3 | 3/3 | 13 | 8 |
| | $10^{-4}$ | 1/5 | 0/5 | 1/3 | 0/3 | 1 | 0 |
| | $10^{-5}$ | 0/5 | 0/5 | 0/3 | 0/3 | 0 | 0 |
| | Non-inoculated control | 0/5 | 0/5 | 0/3 | 0/3 | 0 | 0 |
| Unvaccinated control | $10^0$ | 4/5 | 3/5 | 3/3 | 3/3 | 86 | 67 |
| | $10^{-1}$ | 3/5 | 2/5 | 3/3 | 3/3 | 61 | 40 |
| | $10^{-2}$ | 4/5 | 1/5 | 3/3 | 3/3 | 33 | 25 |
| | $10^{-3}$ | 4/5 | 1/5 | 3/3 | 3/3 | 14 | 8 |
| | $10^{-4}$ | 2/5 | 0/5 | 2/3 | 0/3 | 3 | 0 |
| | $10^{-5}$ | 0/5 | 0/5 | 0/3 | 0/3 | 0 | 0 |
| | Non-inoculated control | 0/5 | 0/5 | 0/3 | 0/3 | 0 | 0 |

*The birds were necropsized for gross and/or microscopic pathological changes at three weeks post-inoculation **JM virus recovery from chicken kidney cell cultures at three weeks post-inoculation
***The average plaques of total samples In each case, 100 $CID_{50}$ of vaccine was used per chick for initial and booster vaccination. The birds which died did so as a result of the vaccination, illustrating the hazards associated with use of unmodified material compared to the safety of using embryo-passaged material in accordance with the invention.

TABLE IV

| Source of Chicks | Vaccination at One Day | | Booster at Three Weeks | |
|---|---|---|---|---|
| | Cell-Free | Embryo-Passed | Cell-Free | Embryo-Passed |
| N-Line Progeny From Vaccinated Dams | 16/18 | 10/10 | 13/14 | 7/7 |
| N-Line Progeny From Unvaccinated Dams | 7/9 | 10/10 | 7/7 | 7/7 |
| P-Line Progeny From Vaccinated Dams | 13/15 | 15/15 | 10/11 | 12/12 |
| P-Line Progeny From Unvaccinated Dams | 13/18 | 15/15 | 10/11 | 12/12 |

In the above table, the numbers represent number of survivors/number vaccinated for each group.

Some of the survivors from both groups of vaccinates (Cell-free JM-V vaccinated and embryo-passaged material vaccinated) as well as a group of HVT vaccinated birds were subsequently subjected to challenge with 2,000 $LD_{50}$ of JM-V at 6 weeks of age. As seen in the following Table V, both cell-free and embryo-passaged material provided total protection, while HVT provided significant but not total protection as compared to unvaccinated controls. In all cases, the numbers represent survivors/birds tested.

of susceptible P-line chickens vaccinated at day-old and three weeks of age with 2,000 PFU of commercial HVT vaccine or 100 $CEID_{50}$ of vaccine according to the invention, or naturally exposed to field Marek's disease, is shown in FIG. 1. As is apparent from FIG. 1, the immune response resulting from vaccination with the vaccine of this invention is much greater than for unvaccinated birds or birds vaccinated with HVT vaccine.

Figure 2:
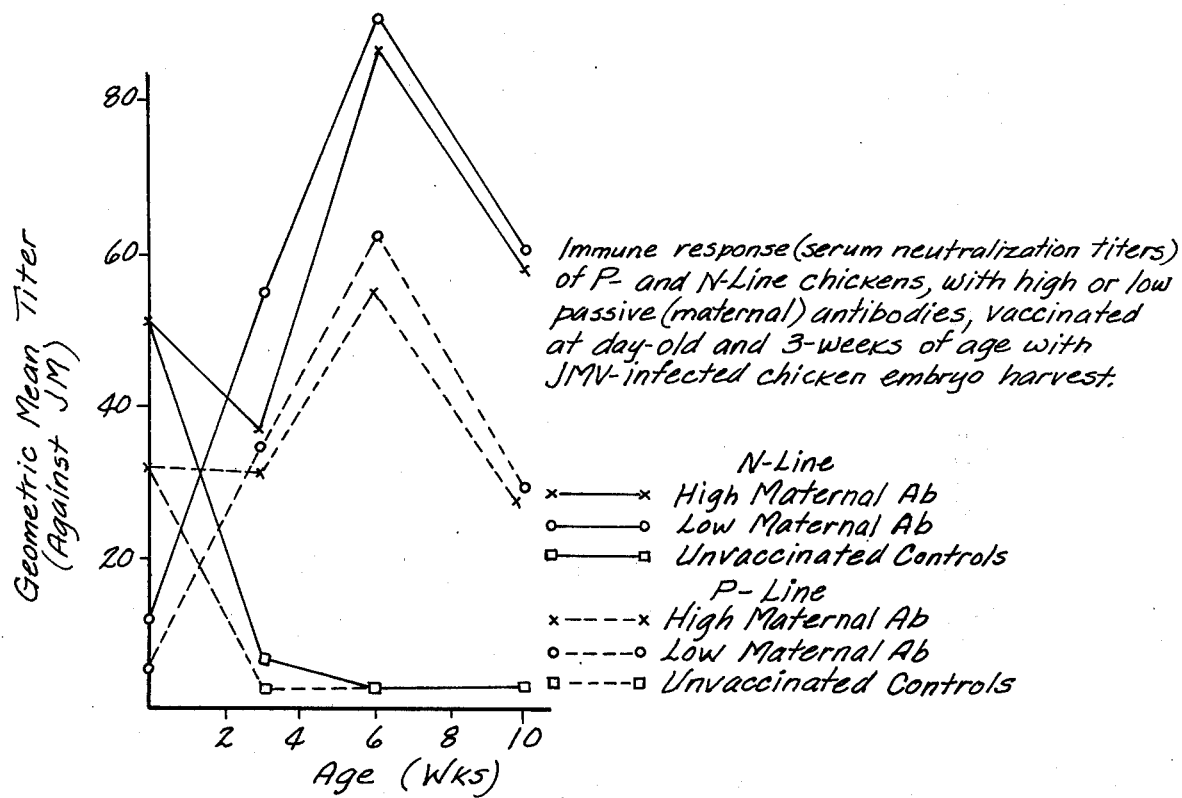

The immune response (serum neutralization titers) of susceptible P-line and resistant N-line chickens with high or low passive (maternal) antibodies, vaccinated at day-old and 3 weeks of age with 0.1 ml. of embryo harvest after 18 and 21 passages respectively through avian embryos starting with blood from a moribund chick previously inoculated with JM-V (VR-736), is illustrated in FIG. 2. As is apparent, the unvaccinated controls, both N and P-line chicks, quickly lost most of their initial immunity and after three weeks had very low antibody levels.

Figure 3:
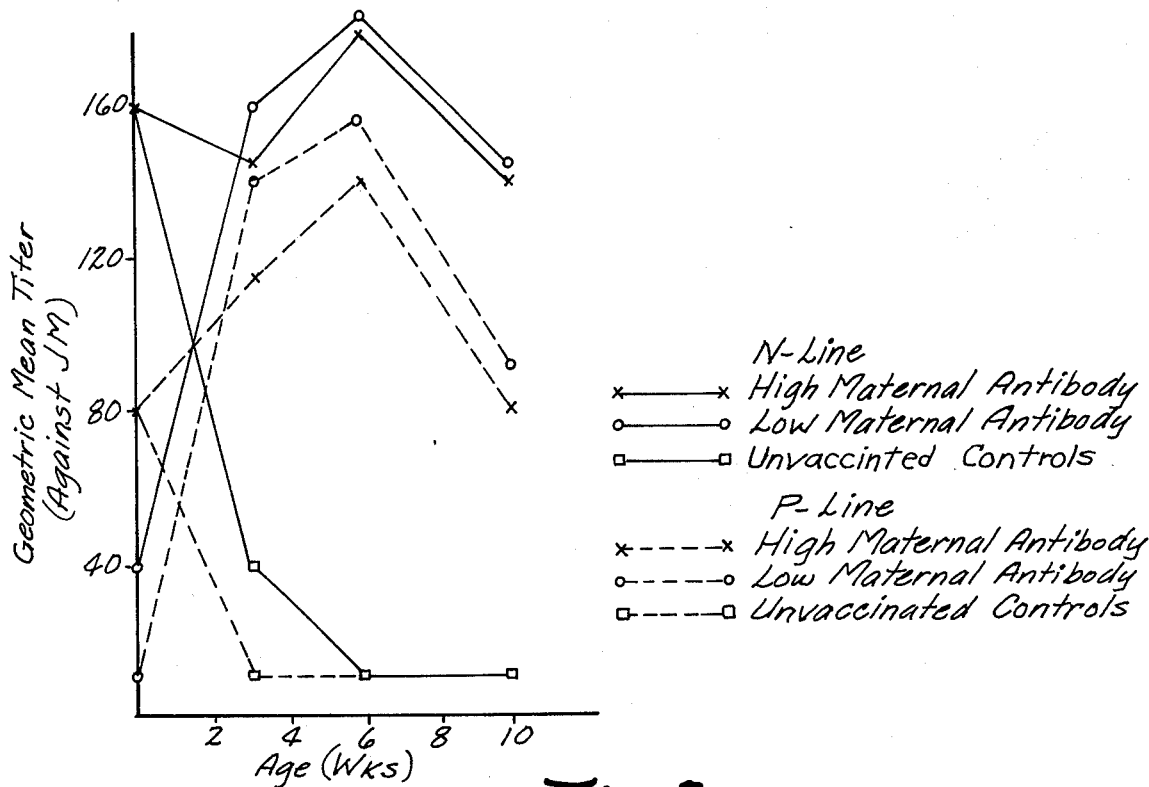

FIG. 3 illustrates the indirect fluorescent antibody titers of P-line and N-line chicks, with high or low passage (maternal) antibodies, vaccinated at day-old and at 3 weeks of age with embryo harvests of vaccine derived from JM-V (VR-736) in accordance with the invention. As is apparent, the antibody titer is much higher for birds vaccinated with the vaccine of this invention than for unvaccinated birds.

Figure 4:
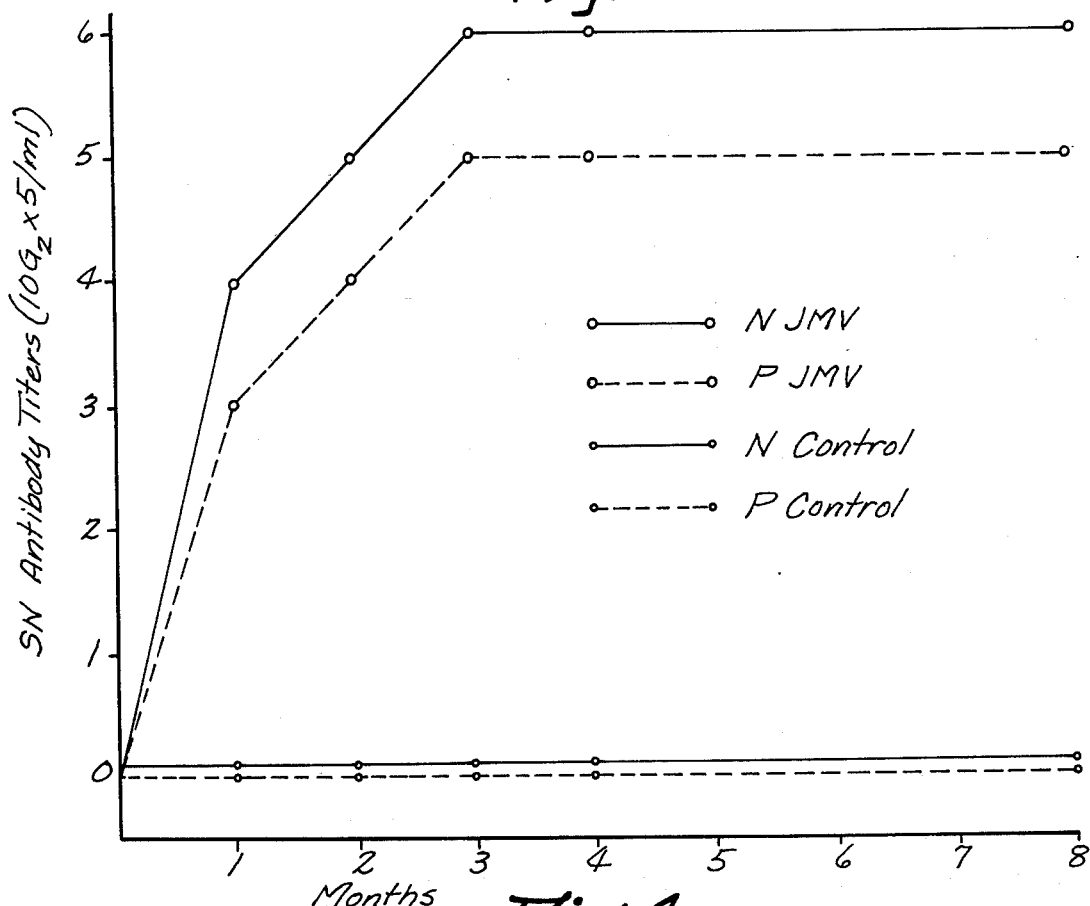

FIG. 4 illustrates the levels and duration of active immune response, measured by serum neutralization test against JM virus in vitro, of 18 month old P and N-line chickens inoculated by intra-muscular injection of 100 $CEID_{50}$ of vaccine prepared as a cell-free JM-V material. The levels of immune response are seen to be much higher for both P and N-line chickens after vaccination, and the immune response is seen to be maintained over a long duration, again illustrating the antibody response to inoculation with JM-V derived material.

The vaccine according to this invention may be handled by conventional procedures. As noted above, the harvested embryo yolk sac material after many passages starting with JM-V (VR-736) may be used directly, such as by withdrawing 0.1 ml. of material and injecting it into a vaccinate. This material has a titer of the order of $10^5$ $CEID_{50}$ per cc.

For commercial operations, the harvested yolk sac material would preferably be stabilized with any of many available conventional stabilizing compositions, such as with an equal volume of a stabilizer comprised of 7% DMSO, 10% bovine fetal calf serum, and the remainder medium 199. The temperature of the stabilized harvested material would be lowered at a rate of 1°/minute to −60°C and then stored in liquid nitrogen. Just prior to use, the frozen stabilized material would be thawed quickly in water at room temperature, and then diluted with a pharmaceutically acceptable diluent such as one-quarter strength tryptose phosphate broth or phosphate buffered saline at pH 7.2. The amount of diluent is typically 100 – 1,000 times the volume of thawed material, depending on titer of the vaccine and the manner in which it is to be used.

The vaccine could alternatively be lyophilized for storage and handling convenience, and the vaccine in cell-free form can be obtained by disruption of the cell, such as by sonication, freeze-thaw, etc.

The vaccine may be administered by a variety of methods, including subcutaneous, intra-muscular or intra-abdominal injection, in which cases about 10 – 100 chicken embryo infective doses 50 percent would be recommended, or by any of the natural routes of infection, such as per os, respiratory system or eye, in which cases 100 – 1,000 $CEID_{50}$ might be needed for effective results. An especially convenient method includes forming an aerosol spray containing the vaccine in a confined space enclosing the birds to be vaccinated.

A particularly important feature of this invention is that a JM-V agent (VR-736) which is capable of inducing exceptionally high antibody response in a host bird has been processed until it has lost its pathogenicity, while retaining its ability to induce antibody response in a host bird, thereby providing a vaccine which is safe as well as effective.

The above detailed description of preferred embodiments of the invention is for the purpose of describing the present best known versions of the invention, and is not to be considered as limiting the invention, which is to be defined by the appended claims.

Having thus described the invention, what is claimed is:

1. Process for preparing vaccine for immunizing poultry against JM and serologically like strains of Marek's disease comprising the steps of producing a virulent strain of modified Marek's disease virus (JM-V) by the multiple serial passage of JM strain of field Marek's disease virus through humoral antibody producing tissue of live young chicks, continuing said serial passage until said virus becomes highly immunogenic and pathogenic as evidenced by lymphoblastic leukemia and mortality of birds within ten days post-inoculation, the immunogenicity of said modified virus (JM-V) being evidenced by development in chickens inoculated with the modified virus of antibody levels in the range of 10–350 serum neutralization titers per milliliter, and thereafter attenuating the pathogenicity of said modified virus by serially passing the same through yolk sacs of avian embryos until a vaccine is obtained which is non-contagious, aviremic and non-pathogenic or substantially so but remains highly immunigenic to Marek's disease virus, whereby poultry inoculated with said vaccine is able to withstand infectous challenge of said JM-V and JM strain of Marek's disease virus.

2. Process of preparing vaccine for immunizing poultry as set forth in claim 1 wherein said highly pathogenic agent is obtained by the multiple passage of JM strain field Marek's disease virus through live chickens for at least 100 passages, the first several of said passages involving the use of said selected tissues, the blood of said chickens being used for the remainder of said passages, and in which the attenuation of said highly pathogenic agent is carried out by at least 40 serial passages through avian embryos.

3. Process of preparing vaccine for immunizing poultry as set forth in claim 1 wherein said JM strain field Marek's disease virus is rendered highly immunogenic and pathogenic by the rapid multiple serial passage through tissues extracted from live chickens infected with Marek's disease virus of one or more of the following organs in which antibodies are produced: spleen, bone marrow, liver and kidneys; using such tissues for a number of said serial passages and for the remainder of said serial passages using whole blood extracted from moribund chickens until said agent becomes highly immunogenic and pathogenic and thereafter attenuating the pathogenicity of said modified virus by serially passing the same through yolk sacs of avian embryos, each passage being 5 to 10 days duration.

4. Process of preparing vaccine for immunizing poultry as set forth in claim 1 wherein said highly pathogenic agent is designated by ATCC No. VR-736.

5. Process of preparing vaccine for immunizing poultry as set forth in claim 1 wherein the embryo material is harvested about one week after inoculation with the agent and is repassed into the yolk sac of avian embryos for about 1 week per passage until a material is obtained which is non-pathogenic for day-old chicks.

* * * * *